US009278047B2

(12) United States Patent
Stan

(10) Patent No.: US 9,278,047 B2
(45) Date of Patent: Mar. 8, 2016

(54) ACUPUNCTURE NEEDLE DELIVERY SYSTEM

(71) Applicant: John Dumitru Stan, Vancouver (CA)

(72) Inventor: John Dumitru Stan, Vancouver (CA)

( * ) Notice: Subject to any disclaimer, the term of this patent is extended or adjusted under 35 U.S.C. 154(b) by 0 days.

(21) Appl. No.: 14/585,673

(22) Filed: Dec. 30, 2014

(65) Prior Publication Data

US 2015/0209225 A1 Jul. 30, 2015

Related U.S. Application Data

(63) Continuation of application No. 12/757,941, filed on Apr. 9, 2010, now abandoned.

(30) Foreign Application Priority Data

Apr. 1, 2010 (CA) ...................................... 2698955

(51) Int. Cl.
*A61B 17/34* (2006.01)
*A61H 39/08* (2006.01)

(52) U.S. Cl.
CPC .................................... *A61H 39/083* (2013.01)

(58) Field of Classification Search
CPC ........... A61B 17/3468; A61B 17/3403; A61H 39/04; A61H 39/08
See application file for complete search history.

(56) References Cited

U.S. PATENT DOCUMENTS 3,905,375 A 9/1975 Toyama
4,139,011 A 2/1979 Benoit et al.
4,161,943 A 7/1979 Nogier
4,479,496 A 10/1984 Hsu
4,580,566 A 4/1986 Hsu
4,907,590 A 3/1990 Wang et al.
5,089,001 A 2/1992 Hwang
5,569,288 A * 10/1996 Yoon ............................ 606/185
5,624,460 A 4/1997 Yoo
6,231,584 B1 5/2001 Gavronsky
6,551,339 B2 4/2003 Gavronsky (Continued)

FOREIGN PATENT DOCUMENTS

CN 201257135 6/2009
CN 201370749 12/2009

(Continued)

OTHER PUBLICATIONS

Machine translation of Takeshi (JP 2004-159851) obtained Jan. 3, 2014.
Canadian Patent Application Serial No. 2,698,955, Office Action dated Aug. 1, 2011.

(Continued)

*Primary Examiner* — Jonathan W Miles
(74) *Attorney, Agent, or Firm* — Lane Powell PC; Kevin D. Jablonski

(57) ABSTRACT

An acupuncture needle and delivery system that facilitates the sanitary insertion and handling of the acupuncture needle in all orientations, and that does not impede the performance of the various post-insertion procedures of the sort commonly used by acupuncture practitioners. In a fully assembled pre-use state, the device includes an acupuncture needle having a filiform shaft and an enlarged head portion, an insertion tube accommodating at least the filiform shaft of the acupuncture needle to protect the filiform shaft from contamination, a stabilization sleeve slidably engaging the outer surface of the insertion tube, and retainer means for releasably securing the acupuncture needle within the insertion tube.

1 Claim, 5 Drawing Sheets

(56) References Cited

U.S. PATENT DOCUMENTS

| | | | | |
|---|---|---|---|---|
| 2004/0065334 | A1 * | 4/2004 | Yoo | 128/907 |
| 2005/0267507 | A1 * | 12/2005 | Kao | 606/189 |
| 2007/0129744 | A1 | 6/2007 | Teichert et al. | |
| 2009/0043329 | A1 * | 2/2009 | Teichert et al. | 606/189 |

FOREIGN PATENT DOCUMENTS

| | | |
|---|---|---|
| JP | 2004-159851 | 6/2004 |
| JP | 2006-314726 | 11/2006 |
| JP | 2008-245889 | 10/2008 |
| KR | 2007-0051390 | 5/2007 |
| TW | M281626 | 12/2005 |
| TW | M321781 | 11/2007 |

OTHER PUBLICATIONS

Office Action dated Dec. 19, 2011, U.S. Appl. No. 12/757,941, filed Apr. 9, 2010.

Final Office Action dated Jul. 23, 2012, U.S. Appl. No. 12/757,941, filed Apr. 9, 2010.

Office Action dated Jul. 17, 2013, U.S. Appl. No. 12/757,941, filed Apr. 9, 2010.

Final Office Action dated Jan. 9, 2014, U.S. Appl. No. 12/757,941, filed Apr. 9, 2010.

Office Action dated Apr. 18, 2014, U.S. Appl. No. 12/757,941, filed Apr. 9, 2010.

Final Office Action dated Aug. 5, 2014, U.S. Appl. No. 12/757,941, filed Apr. 9, 2010.

* cited by examiner

ACUPUNCTURE NEEDLE DELIVERY SYSTEM

TECHNICAL FIELD

The present disclosure relates to acupuncture, and more particularly to acupuncture needles and to delivery systems and methods for the sanitary insertion and handling thereof during the performance of acupuncture treatments.

BACKGROUND

Acupuncture is gaining wide acceptance as a medical treatment for a variety of health conditions, and has become widely integrated into health care systems throughout North America. By way of general overview, acupuncture involves the insertion of a filiform needle (at least the shaft of which is typically constructed of medical grade stainless steel) to a target depth below the dermis of the skin at a predetermined sensitive point, and the performance of various additional procedures selected to stimulate a positive change in the health condition of a patient. These additional procedures may, for example, involve heating the needle with a heat source (commonly known as "moxibustion"), applying electrical stimulation to the needle, such as by attaching the needle to a milliamp or microamp stimulator, and/or the use of various manual manipulative techniques such as thrusting, angling and vibrating the needle.

To minimize patient discomfort, the acupuncture needle is typically first quickly "set" through the dermal layer of the patient's skin, and then further inserted through the skin into the body of the patient to a target depth of up to several centimeters, depending upon the application and on the region of the body being treated. In many cases, the acupuncture treatment may be preformed on a recumbent patient that has been positioned so as to facilitate the practitioner's access to the predetermined sensitive point. However, in some instances, such as when patients have circulatory or neurological limitations, this is not possible and the acupuncture needle must be set and inserted horizontally, or even from below.

Great care must be taken to maintain sterility of the acupuncture needle throughout the entire acupuncture treatment process in order to protect both the patient and the practitioner from possible contamination, and acupuncture needle delivery techniques have accordingly evolved over the years from simple free hand insertion and manipulation to the use of insertion tube-assisted delivery systems intended to assist with the maintenance of sanitary conditions (and in some instances to facilitate consistent setting of the acupuncture needle). As is discussed further below, the use of an insertion tube surrounding the needle shaft facilitates sanitary pre-use initial handling and setting of an acupuncture needle by a practitioner. Once the needle has been set, the insertion tube is generally discarded in order to permit the further insertion and manipulation of the needle at the target depth.

Additional sanitary challenges often arise, however, during the further insertion and manipulation of the acupuncture needle at the target depth, particularly in situations where the practitioner is inserting the needle into scarred, dense, or fibrous tissue (such as in intra-articular insertions in, for example, the knee). In these situations and others, such as where, for example, the needle has a thickness of 0.22 mm or less and a needle length is 35 mm or shorter, or a thickness of 0.22 mm or greater and a length that is 50 mm or longer, the needle is prone to bowing or bending during further insertion and manipulation.

Any such bowing or bending interferes with the practitioner's ability to accurately insert and manipulate the needle, and requires the practitioner to attempt to compensate by initiating time consuming and/or difficult compensatory movements. In many cases, suitable compensation for the bowing or bending of the needle is not easily achievable, and in some cases may not be achievable at all by even the most skilful practitioner unless the practitioner stabilizes the shaft of the needle using a cotton swab or simply his/her fingers. These stabilization techniques compromise the sterility of the needle, and increase the risk of infection.

To address this need for stabilization (and the resulting potential for contamination), acupuncture needle assemblies and delivery systems that additionally provide a grip element have been proposed. However, all known acupuncture needle assemblies and delivery systems that additionally provide a grip element to facilitate stabilization of the needle during insertion and manipulation fail to adequately address the need for such stabilization when the needle is inserted horizontally or from below the predetermined sensitive point, or fail to adequately accommodate the performance of various stimulative procedures. In addition, many of the known needle assemblies and delivery systems are relatively difficult to manufacture and to use.

By way of example, U.S. Pat. No. 5,624,460 to Yoo describes an acupuncture needle assembly that includes a "guide pipe" (i.e. an insertion tube) and a paper, rubber or foamed resin "grip pipe" that is located within the guide pipe and that immediately surrounds the needle shaft about 3-5 mm from the end portion of the needle head. As with a conventional insertion tube-assisted delivery system, the guide pipe facilitates the sanitary pre-use initial handling and setting of the needle, and is discarded once the needle has been set. A practitioner may then grasp the grip pipe to stabilize the needle during the acupuncture stimulus, and use the grip pipe to withdraw the needle from the patient after use.

However, since the Yoo grip pipe is formed of paper, rubber or foamed resin, and since it immediately surrounds the shaft of the needle, which has an internal diameter that is smaller than that of the handle or upper "grip portion" of the needle itself, the Yoo grip pipe cannot readily be removed from the needle during use, and would accordingly impede procedures requiring a practitioner to heat or electrify the needle. For example, the moxibustion technique known as "sparrow pecking" requires a practitioner to heat the acupuncture point and needle with an external heat source to stimulate circulation and immune function. It is important in performing this technique to bring the heat source to the point were the heat is intense but tolerable in a "coming and going" process (i.e. in a "pecking" manner), and to achieve this the heat source must be brought as close as possible to the needle and to the skin to generate a strong heat reaction. Since the Yoo grip pipe is immediately associated with the needle shaft and cannot readily be removed, it may have an insulatory effect between the needle and the heat source (and may itself melt or burn if brought too close to the heat source), and thereby limit the effectiveness of this type of procedure. Additionally, in some scenarios, the treatment target depth may require the needle to be inserted up to 90% or so of it's overall length. Since the Yoo needle assembly does not provide for removal of the grip pipe during use, the grip pipe also limits the depth to which a practitioner may insert the Yoo needle.

Published U.S. patent publication Ser. No. 11/292,025 to Teichert et al. (U.S. Patent Publication No. 2007/0129744), the disclosure of which is hereby fully incorporated by reference, describes an acupuncture needle guide assembly that comprises an acupuncture needle with a shaft and a needle handle, a guiding tube (i.e. an insertion tube) accommodating the acupuncture needle before use and providing guidance for setting the acupuncture needle, a holding tube being arranged within the guiding tube and providing a cover for the needle shaft, and a destructible or detachable connector fixing the holding tube between the needle handle and an inner wall of the guiding tube until the connector is removed or broken. The holding tube has an inner diameter that is greater than the diameter of the needle shaft, and preferably has an inner diameter that is greater than the outer diameter of the needle handle in order to permit the holding tube to be removed from the needle after insertion thereof into the body. In use, the assembly is first positioned on the skin of the patient to be treated, and the acupuncture needle is then released by removing or breaking the connector. Upon removal or destruction of the connector, the holding tube drops down the shaft of the needle towards the tip thereof under the effect of gravity, and is manually gripped by the practitioner after the guiding tube is withdrawn to facilitate stabilization during the further insertion and manipulation of the needle.

Although the "loose" fit of the holding tube vis-à-vis the needle of the Teichert et al. assembly permits the holding tube to be removed during use and thereby addresses some of the shortcomings of the Yoo assembly, the inability of a practitioner to control the position of the holding tube after the connector is removed or broken, but prior to removal of the guiding tube, makes it generally unsuitable for use in horizontal orientations, or in situations where the needle must be set and inserted from below the predetermined sensitive point.

There accordingly exists a need for an improved acupuncture needle and delivery system that facilitates the sanitary insertion and handling of the acupuncture needle in all orientations, and that does not impede the performance of the various post-insertion procedures of the sort that are commonly used by acupuncture practitioners to stimulate a positive change in the health condition of a patient. Since the need for stabilization of the needle shaft is situation dependant, provision of an improved acupuncture needle and delivery system in which the implementation of the stabilizing feature is optional and does not commit the practitioner to a predefined insertion process would also be beneficial.

SUMMARY

This summary is not an extensive overview intended to delineate the scope of the subject matter that is described and claimed herein. The summary presents aspects of the subject matter in a simplified form to provide a basic understanding thereof, as a prelude to the detailed description that is presented below. Neither this summary nor the following detailed description purports to define or limit the invention; the invention is defined only by the claims.

In embodiments of the present subject matter, there is provided an acupuncture needle delivery system comprising, in its fully assembled pre-use state, an acupuncture needle having a filiform shaft and an enlarged head portion, an insertion tube having an axial length that is less than the axial length of the acupuncture needle, the insertion tube being adapted to accommodate at least the filiform shaft of the acupuncture needle to protect the filiform shaft from contamination, a stabilization sleeve slidably engaging the outer surface of the insertion tube, and retainer means for releasably securing the acupuncture needle within the insertion tube.

Preferably, the axial length of the insertion tube is between roughly 2 mm and 5 mm less than the axial length of the acupuncture needle, and the axial length of the stabilization sleeve is between roughly ¼ to ½ of the axial length of the insertion tube.

Also provided is a method of introducing an acupuncture needle into a body to be treated, the method comprising the steps of: providing the acupuncture needle delivery system according to the present disclosure; positioning the insertion tube at a predetermined sensitive point on the skin of a patient to be treated; sliding the stabilization sleeve down to abut the skin of the patient; releasing the acupuncture needle within the insertion tube by removing or destroying the retainer means; setting the filiform shaft of the acupuncture needle into or through the dermal layer of the skin; removing the insertion tube to permit the further insertion of the acupuncture needle; optionally grasping the stabilization sleeve while further inserting the acupuncture needle to a predetermined target depth; and optionally removing or discarding the stabilization sleeve.

Since the stabilization sleeve is slidably engaged around the outer surface of the insertion tube, it may readily be discarded prior to or at any point during the acupuncture treatment process, thereby providing the option to use the stabilization sleeve in circumstances where stabilization is desired or required, while avoiding possible interference that may be caused by the presence of a stabilization sleeve during the performance of the various post-insertion procedures of the sort that are commonly used by acupuncture practitioners. The slidable engagement of the stabilization sleeve around the outer surface of the insertion tube also enables the sanitary insertion and handling of the acupuncture needle in all orientations.

BRIEF DESCRIPTION OF THE DRAWINGS

For a fuller understanding of the nature and advantages of the disclosed subject matter, as well as the preferred mode of use thereof, reference should be made to the following detailed description, read in conjunction with the accompanying drawings. In the drawings, like reference numerals designate like or similar steps or components.

DETAILED DESCRIPTION OF SPECIFIC EMBODIMENTS

Specific embodiments of the disclosed apparatus and method will now be described with reference to the drawings. Nothing in this detailed description is intended to imply that any particular component, feature, or step is essential to the invention.

Figure 1:
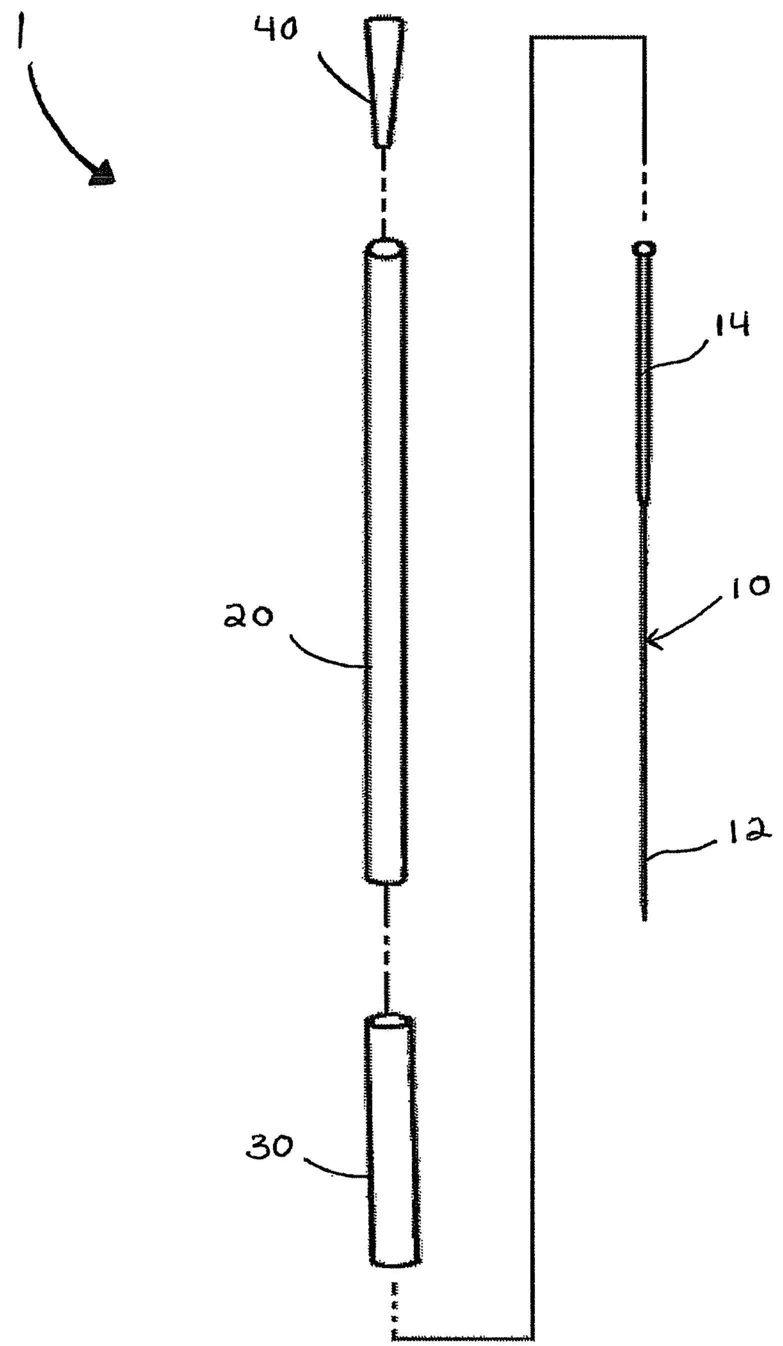
FIG. 1 is an exploded perspective view of an acupuncture needle and delivery system in accordance with an embodiment of the presently disclosed subject matter.
Figure 2:
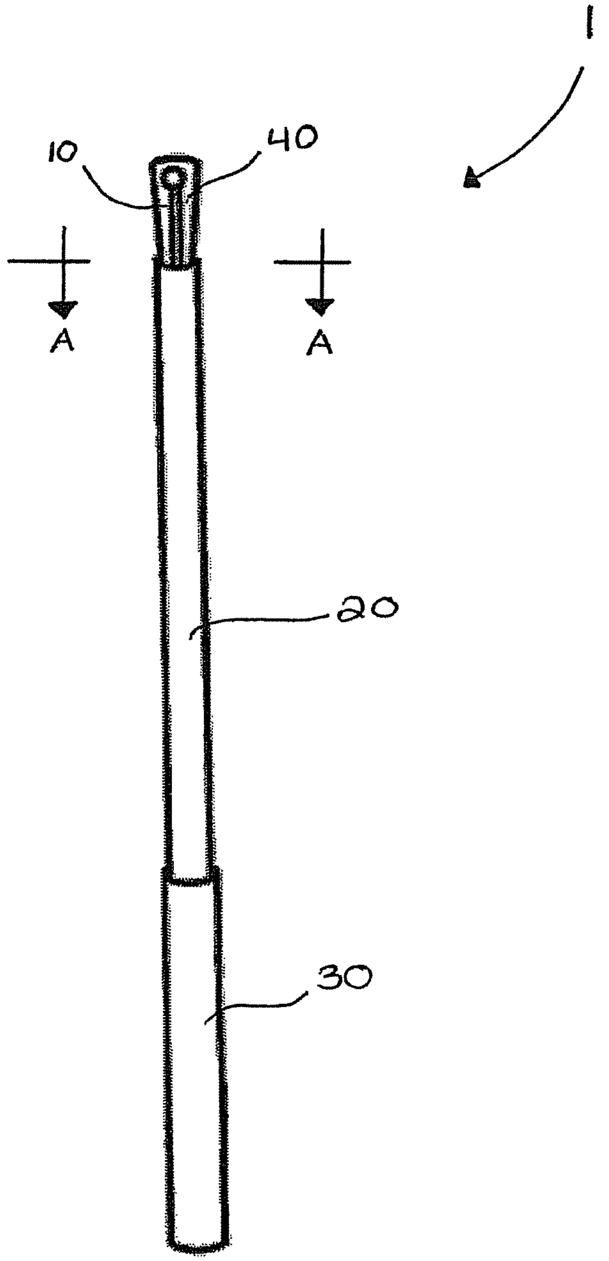
FIG. 2 is an acupuncture needle and delivery system in accordance with an embodiment of the presently disclosed subject matter, shown in the fully assembled pre-use state thereof.
Figure 3:
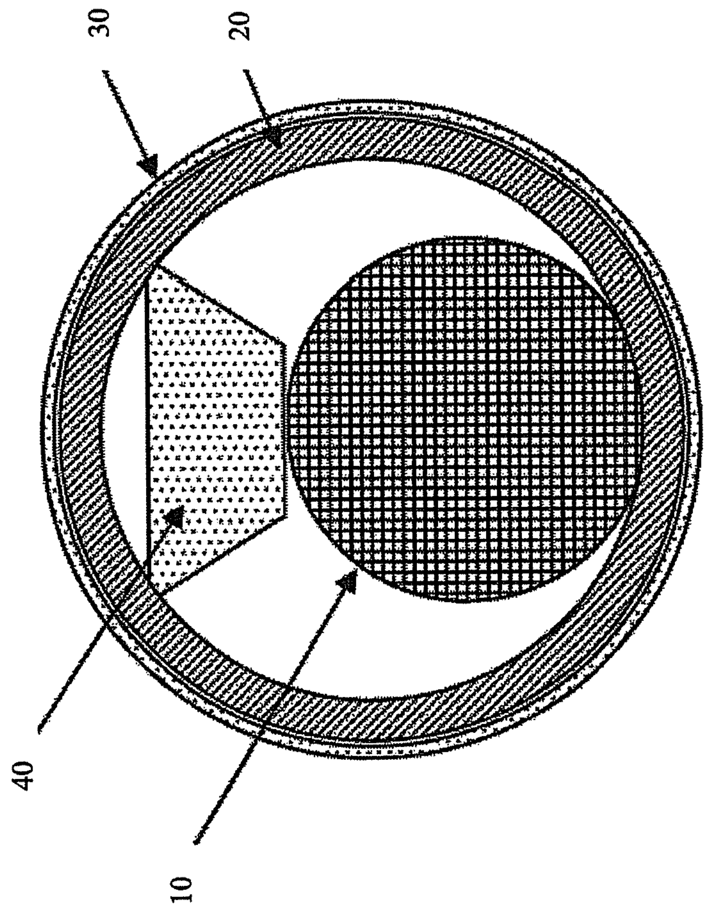
FIG. 3 is an enlarged sectional view of FIG. 2, taken along line A-A; and, FIGS. 4A-4G are perspective views of several phases of setting and inserting an acupuncture needle using an acupuncture needle and delivery system in accordance with an embodiment of the presently disclosed subject matter.

Referring now to FIGS. 1 to 3, an embodiment of an acupuncture needle and delivery system in accordance with the present disclosure is generally designated therein with reference numeral 1, and comprises a needle 10, an insertion tube 20, a stabilizing sleeve 30, and a retainer 40.

Needle 10 is of generally conventional construction for an acupuncture needle, and comprises filiform shaft 12 and an enlarged head portion 14 to facilitate handling by a practitioner/user. In preferred embodiments, the shaft 12 and the head portion 14 are formed from medically approved surgical stainless steel, or from other suitable heat- and electricity-conducting materials known to those of skill in the art, in order to accommodate moxibustion and/or electrical stimulation procedures.

FIG. 1 illustrates the acupuncture needle and delivery system in its fully assembled pre-use state, in which at least the filiform shaft 12 of needle 10 is surrounded by insertion tube 20 in order to protect shaft 12 from contamination. The inner diameter or insertion tube 20 is suitably selected with reference to the diameter of head portion 14 of needle 10, and is sufficiently large to permit needle 10 to freely slide through insertion tube 20 once retainer 40 has been removed therefrom or destroyed, but not so large as to permit needle 10 to bend or bow excessively under the axial force applied by a user to head portion 14 during the "setting" of needle 10 into or through the dermal layer of a patient's skin.

The axial length of insertion tube 20 is similarly selected with reference to the axial length of needle 10, such that at least part of head portion 14 extends past the end of insertion tube 20 when the acupuncture needle and delivery system is in the fully assembled pre-use state. The entire axial length of shaft 12 is contained within insertion tube 20 in order to protect it from contamination. In preferred embodiments, insertion tube 20 is shorter than needle 10 by roughly the typical thickness of the dermal layer of a patient's skin. Most preferably, the axial length of insertion tube 20 is selected to be between 2 mm and 5 mm shorter than the axial length of needle 10.

Insertion tube 20 may be formed from any suitable material known to those of skill in the art, and in preferred embodiments is formed from a plastic material, such as polyethylene, that may be economically manufactured, and that may be sterilized without degradation of the material during sterilization by trade-recognized methods such as the use of gamma radiation or ethylene oxide sterilization. In preferred embodiments, insertion tube 20 has a circular cross-section in order to minimize the amount of material required for manufacture. However, it will be appreciated by those of skill in the art that insertion tube 20 may be formed with a cross-section of any desired shape, such as, for example, square or triangular. Most preferably, insertion tube 20 is formed from a transparent material in order to facilitate the accurate "setting" of needle 10.

Stabilizing sleeve 30 circumferentially surrounds a portion of insertion tube 20 when the acupuncture needle and delivery system is in the fully assembled pre-use state, and has an inner diameter that is selected with reference to the outer diameter of insertion tube 20, such that stabilization sleeve 30 slidably engages the circumferential outer surface of insertion tube 20 in a snug manner that allows a user to easily slide stabilizing sleeve 30 up or down the outer surface of insertion tube 20 during use, but that prevents stabilizing sleeve 30 from freely sliding by itself (such as under the influence of gravity) relative to the outer surface of insertion tube 20 in the absence of any external force applied by a user. Stabilization sleeve 30 may be formed from any suitable material such as paper or plastic, and in preferred embodiments is formed from a resilient material that may be economically manufactured, and that may be sterilized without degradation during sterilization by trade-recognized methods such as the use of gamma radiation or ethylene oxide sterilization. If the cross-section of insertion tube 20 is selected to be a shape other than circular, then the cross-sectional shape of corresponding stabilization sleeve 30 is, of course, conformed thereto. The thickness of the material comprising stabilization sleeve 30 is selected such that the sleeve 30 maintains its shape and form in the absence of external force applied by a user, but is sufficiently pliable to easily collapse around shaft 12 of needle 10 when grasped by a user during the performance of a stabilization technique.

The axial length of stabilizing sleeve 30 is selected, in part, with reference to the length of needle 10 and the intended use thereof, and in part with reference to the typical width of a human finger and thumb. By way of example, where a needle 10 is to be inserted into scarred, dense or fibrous tissues (which typically requires more significant stabilization than does a needle inserted into softer tissues), a relatively long stabilizing sleeve 30 may be preferred in order to enable the user to grasp the stabilizing sleeve 30 more firmly, or between more than one finger and the thumb. Conversely, where a needle 10 is long and is to be inserted to a very deep target depth in soft tissue, a relatively short stabilizing sleeve 30 (vis-à-vis the overall axial length of needle 10) may be selected. In preferred embodiments, the axial length of stabilizing sleeve 30 is between roughly ¼ to ½ of the axial length of insertion tube 20.

Retainer 40 holds needle 10 in place within insertion tube 20 when the acupuncture needle and delivery system is in the fully assembled pre-use state, and is removed or destroyed by a user when the acupuncture needle and delivery system has been positioned over a predetermined sensitive point on the skin of a patient in order to enable the needle 10 to be set into or through the dermal layer of the patient's skin. As is best seen in FIG. 3, retainer 40 comprises in preferred embodiments a removable wedge inserted in the end of the insertion tube 20 adjacent head portion 14 of needle 10 to prevent movement thereof relative to insertion tube 20 until retainer 40 is removed or destroyed. In the alternative, retainer 40 may comprise adhesives, handles, or connectors of any suitable sort known to those of skill in the art.

By way of example and not limitation, several phases of a typical use of the presently-disclosed acupuncture needle and delivery system 1 to insert and stabilize needle 10 in the body of a patient are illustrated in FIGS. 4A-4G. For ease of understanding, FIGS. 4A-4G are oriented vertically, showing the acupuncture needle and delivery system 1 in a generally vertical orientation above the patient. It will, however, be readily understood by those of skill in the art that the acupuncture needle and delivery system 1 may readily be used to equal advantage in any orientation, including horizontally or from below the patient. It will also be readily appreciated by those of skill in the art that FIGS. 4A-4G illustrate the insertion and stabilization of needle 10 in a case where stabilization is desired or required, and that in cases where stabilization is not desired or required, stabilization sleeve 30 may simply be removed and discarded prior to or at any stage of use.

Figure 4A:
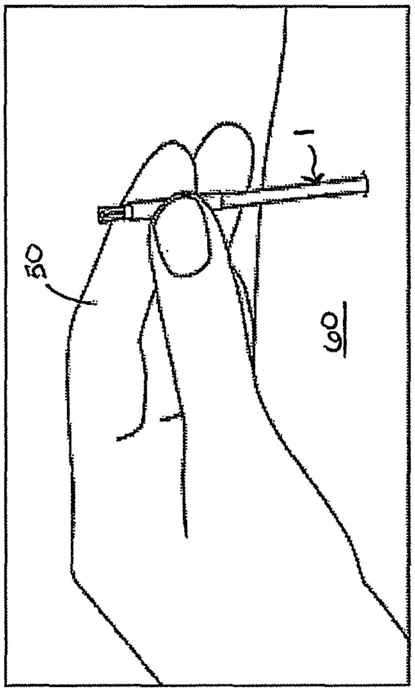
Figure 4B:
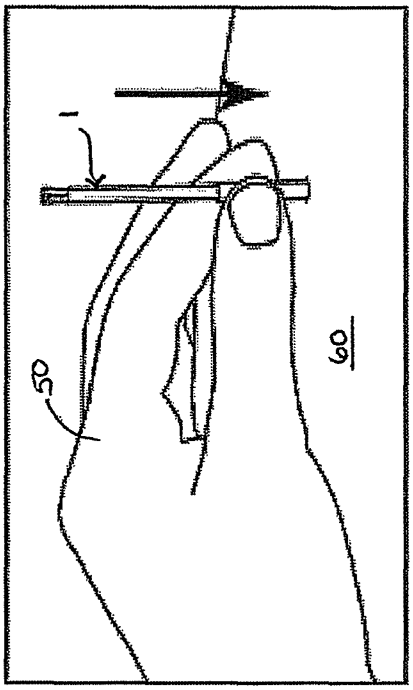
Figure 4C:
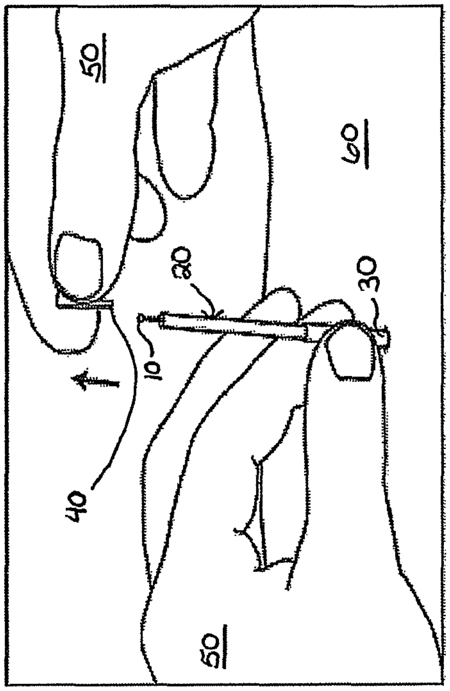

Turning now to FIG. 4A, acupuncture needle and delivery system 1 is illustrated as held by practitioner 50 in its fully assembled pre-use state, and positioned at a predetermined sensitive point on the skin 60 of the body of a patient to be treated. In FIG. 4B, stabilization sleeve 30 is slid down to abut the skin 60, and in FIG. 4C, retainer 40 is removed or destroyed in order to permit the relative movement of needle 10 within insertion tube 20.

Figure 4D:
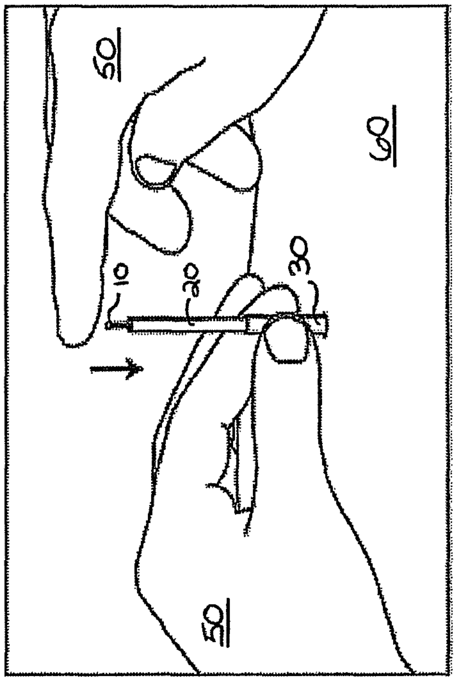
Figure 4F:
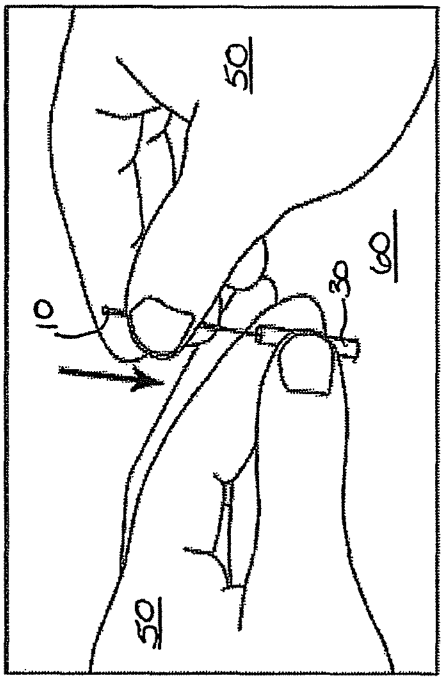
Figure 4E:
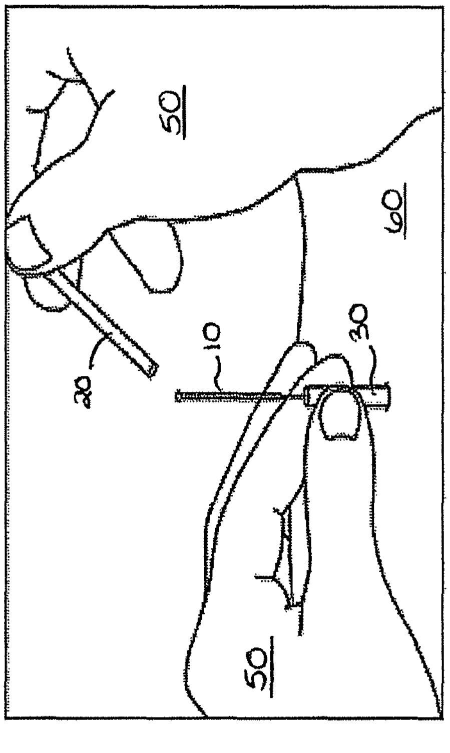
Figure 4G:
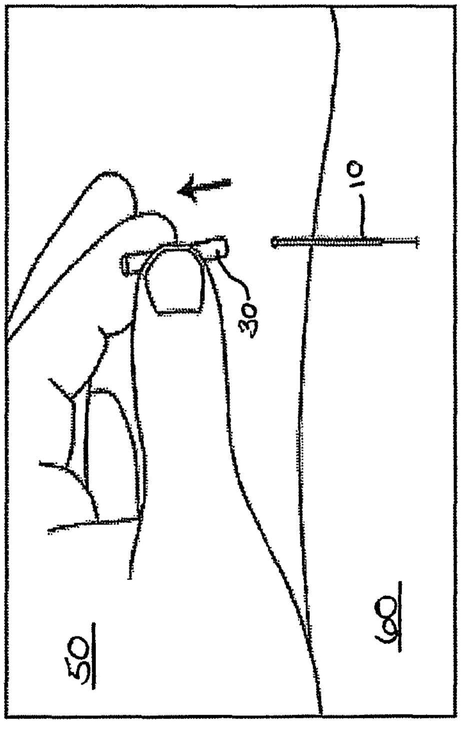

FIG. 4D illustrates the "setting" of needle 10 into or through the dermal layer of skin 60 with a quick tap on head portion 14 of needle 10 by practitioner 50, and FIG. 4E illustrates the removal of insertion tube 20 to permit the further insertion of needle 10. As shown in FIG. 4F, stabilization tube 30 is then used by practitioner 50 to assist in the guidance of needle 10 to a predetermined target depth, and finally, as illustrated in FIG. 4G, stabilization tube 30 may optionally be removed and discarded.

The present description includes the best presently contemplated mode of carrying out the subject matter disclosed and claimed herein, and is made for the purpose of illustrating the general principles of the subject matter and not be taken in a limiting sense; the subject matter can find utility in a variety of implementations without departing from the scope of the disclosure made, as will be apparent to those of skill in the art from an understanding of the principles that underlie the subject matter.

I claim:

1. A method of introducing an acupuncture needle into a body to be treated, said method comprising the steps of:

providing an acupuncture needle delivery system having:

an acupuncture needle having a filiform shaft and an enlarged head portion;

an insertion tube having an axial length that is less than the axial length of the acupuncture needle, said insertion tube being adapted to accommodate at least the filiform shaft of the acupuncture needle to protect the filiform shaft from contamination;

a stabilization sleeve slidably engaging the outer surface of the insertion tube;

and retainer means for releasably securing the acupuncture needle within the insertion tube;

positioning the insertion tube at a predetermined sensitive point on the skin of a patient to be treated;

sliding the stabilization sleeve down to abut the skin of the patient;

releasing the acupuncture needle within the insertion tube by removing or destroying the retainer means;

setting the filiform shaft of said acupuncture needle into or through the dermal layer of the skin; removing said insertion tube to permit the further insertion of said acupuncture needle;

grasping said stabilization sleeve while further inserting said acupuncture needle to a predetermined target depth; and removing or discarding said stabilization sleeve.

* * * * *